US010893391B1

(12) United States Patent
Friedman et al.

(10) Patent No.: US 10,893,391 B1
(45) Date of Patent: Jan. 12, 2021

(54) TRACKING AND MONITORING SYSTEM

(71) Applicants: Lindsay P. Friedman, Russell, OH (US); Kevin Darrah, Medina, OH (US)

(72) Inventors: Lindsay P. Friedman, Russell, OH (US); Kevin Darrah, Medina, OH (US)

(73) Assignee: Lindsay Friedman, Russell, OH (US)

( * ) Notice: Subject to any disclaimer, the term of this patent is extended or adjusted under 35 U.S.C. 154(b) by 0 days.

(21) Appl. No.: 16/933,856

(22) Filed: Jul. 20, 2020

Related U.S. Application Data

(60) Provisional application No. 62/876,892, filed on Jul. 22, 2019.

(51) Int. Cl.
*H04W 4/029* (2018.01)
*G06Q 10/06* (2012.01)
*G06N 20/00* (2019.01)
*G16H 20/10* (2018.01)
*G06Q 30/00* (2012.01)
*G16H 40/20* (2018.01)
*G06Q 50/26* (2012.01)

(52) U.S. Cl.
CPC ............ *H04W 4/029* (2018.02); *G06N 20/00* (2019.01); *G06Q 10/063114* (2013.01); *G06Q 30/0185* (2013.01); *G06Q 50/26* (2013.01); *G16H 20/10* (2018.01); *G16H 40/20* (2018.01)

(58) Field of Classification Search
CPC .................. H04W 4/029; G06N 20/00; G06Q 10/063114; G06Q 30/0185; G06Q 50/26; G16H 40/20; G16H 20/10; G06T 7/004; G06T 7/20; G08B 13/1908
See application file for complete search history.

(56) References Cited

U.S. PATENT DOCUMENTS

| 9,058,702 | B2* | 6/2015 | Chao | H04W 4/029 |
| 2007/0202888 | A1* | 8/2007 | Brachet | G01S 5/02 |
| | | | | 455/456.1 |
| 2009/0054068 | A1* | 2/2009 | Halkka | H04M 1/72572 |
| | | | | 455/445 |
| 2013/0285836 | A1* | 10/2013 | Proud | H02J 50/12 |
| | | | | 340/870.02 |
| 2018/0025605 | A1* | 1/2018 | Thomas | G07C 9/257 |
| | | | | 455/90.1 |
| 2018/0151054 | A1* | 5/2018 | Pi | G08B 21/245 |
| 2018/0322759 | A1* | 11/2018 | Devdas | A61B 5/0024 |

* cited by examiner

*Primary Examiner* — Nizar N Sivji

(57) ABSTRACT

A system and method for tracking and monitoring persons. To begin, the presence of a user at a location is determined when the userID is identified in the primary input data. The user's motion are determined using the primary input data and the secondary input data when the presence of the user at the location is determined. The position of the user is determined using the secondary input data when the presence of the user is determined. A matching algorithm is used to identify reference data that is similar to the primary input data or secondary input data and thereby determines completion of a user task of the user. transmit, via a communications device communicatively coupled to the control circuit, a notification is transmitted to a user computing device for conveyance via the user interface when completion of the user task is determined.

11 Claims, 4 Drawing Sheets

TRACKING AND MONITORING SYSTEM

CROSS-REFERENCE TO RELATED APPLICATIONS

This application claims priority to U.S. Provisional Application No. 62/876,892 filed Jul. 22, 2019, which is hereby incorporated herein by reference.

FIELD OF THE INVENTION

The present disclosure relates generally to people tracking. More specifically, the present disclosure describes a tracking and monitoring system.

BACKGROUND OF THE INVENTION

To ensure that desired tasks and services are completed or rules and regulations are adhered to can be a time-consuming process when undertaken manually. For example, to ensure compliance with the large number of laws and regulations issued by the Occupational Safety and Health Administration (OSHA) can require not only large teams but also an extended period of time for its completion. In the same vein, ensuring that a task (e.g., administration of medication) occurred at a prescribed time typically requires that the inquirer trust the addressee's (i.e. the person entrusted to perform the task) verbal confirmation.

BRIEF DESCRIPTION OF THE DRAWINGS

Some of the embodiments will be described in detail, with reference to the following figures, wherein like designations denote like members, wherein.

Figure 1:
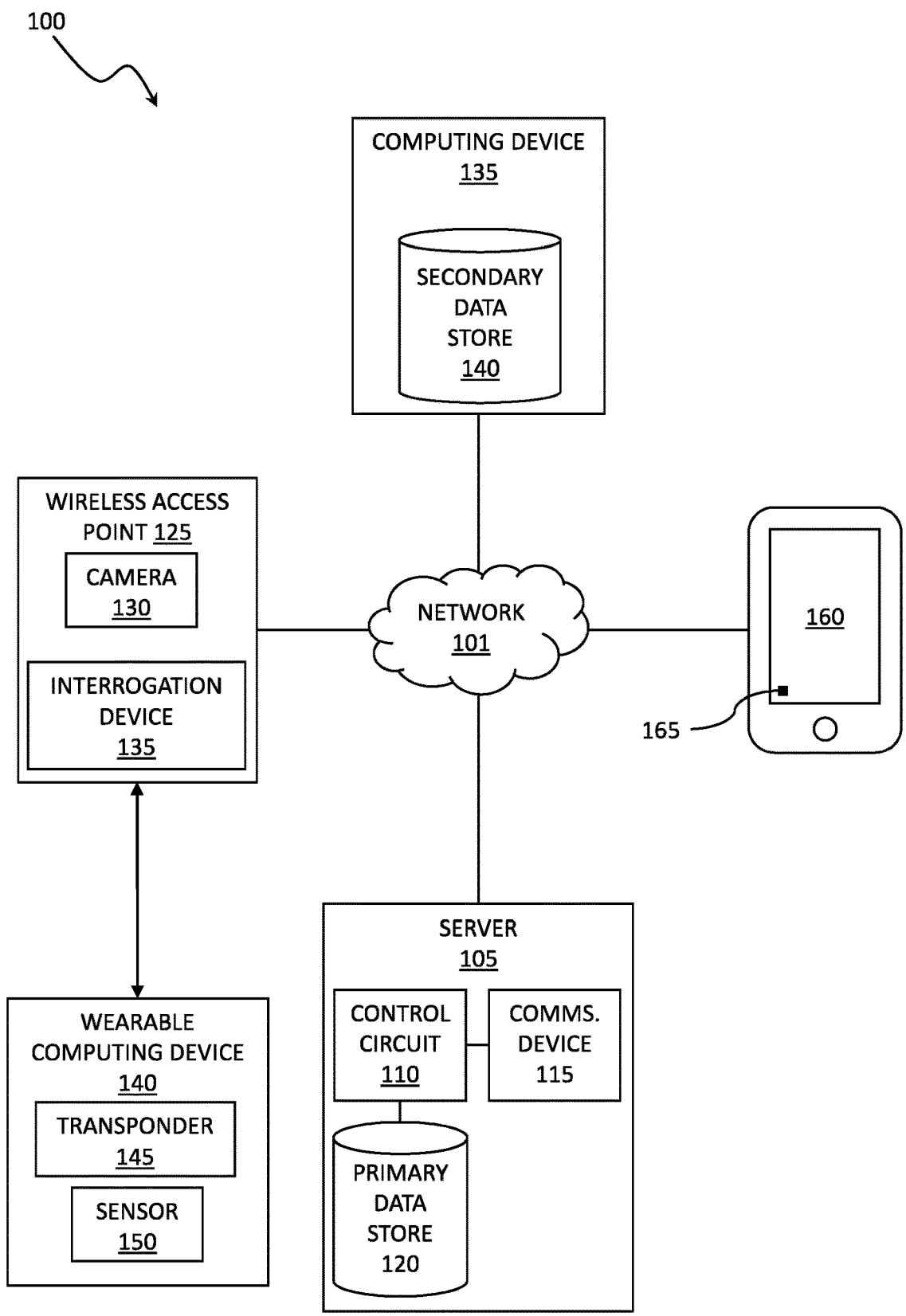
FIG. 1 depicts a block diagram of a system for tracking and monitoring persons, according to some embodiments.

Unless otherwise specifically noted, articles depicted in the drawings are not necessarily drawn to scale.

DETAIL DESCRIPTIONS OF THE INVENTION

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

Other technical advantages may become readily apparent to one of ordinary skill in the art after review of the following figures and description. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise indicated, the drawings are intended to be read together with the specification and are to be considered a portion of the entire written description of this invention. As used in the following description, the terms "horizontal", "vertical", "left", "right", "up", "down" and the like, as well as adjectival and adverbial derivatives thereof (e.g., "horizontally", "rightwardly", "upwardly", "radially", etc.), simply refer to the orientation of the illustrated structure as the particular drawing figure faces the reader. Similarly, the terms "inwardly," "outwardly" and "radially" generally refer to the orientation of a surface relative to its axis of elongation, or axis of rotation, as appropriate. As used herein, the term "dorsal" refers to positions that are located near, on, or towards the upper or top side of a structure.

The present disclosure includes many aspects and features. Moreover, while many aspects and features relate to, and are described in the context of tracking and monitoring systems and methods, embodiments of the present disclosure are not limited to use only in this context.

To ensure that requested tasks and services are completed or rules and regulations are adhered to can be a time-consuming process. For example, to ensure compliance with the large number of laws and regulations issued by the Occupational Safety and Health Administration (OSHA) can require large teams. In the same vein, ensuring that a task (e.g., administration of medication) occurred at a prescribed time typically require that the inquirer trust the addressee's (i.e. the person entrusted to perform the task) verbal confirmation.

The instant disclosure seeks to provide systems and methods that allow users (e.g., administrators, supervisors, as well as similar interested parties) to track a person's current location, duration at specific locations, as well as task verification. Although the instant disclosure is described in the context of a medical setting (e.g., hospital, elder care facility, and similar locations), the systems and methods described herein can be applied to any setting or environment where the tracking and monitoring of persons is desired.

The instant disclosure seeks to utilize machine learning to verify that one or more tasks are completed by the user. Not to be limited by theory, machine learning is the field of study where a computer or computers learn to perform classes of tasks using the feedback generated from the experience or data gathered that the machine learning process acquires during computer performance of those tasks. Typically, machine learning can be broadly classed as supervised and unsupervised approaches, although there are particular approaches such as reinforcement learning and semi-supervised learning which have special rules, techniques and/or approaches. To be sure, the instant disclosure seek to provide systems and methods that use supervised and/or unsupervised machine learning. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabeled data sets. Reinforcement learning is concerned with enabling a computer or computers to interact with a dynamic environment, for example when playing a game or driving a vehicle. Various hybrids of these categories are possible, such as "semi-supervised" machine learning where a training data set has only been partially labelled.

For unsupervised machine learning, there is a range of possible applications such as, for example, the application of computer vision techniques to image processing or video enhancement. Unsupervised machine learning is typically applied to solve problems where an unknown data structure might be present in the data. As the data is unlabeled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships.

When initially configuring a machine learning system, particularly when using a supervised machine learning approach, the machine learning algorithm (e.g., the matching algorithm) can be provided with some training data or a set of training examples, in which each example is typically a pair of an input signal/vector and a desired output value, label (or classification) or signal. The machine learning algorithm analyses the training data and produces a generalized function that can be used with unseen data sets to produce desired output values or signals for the unseen input vectors/signals. The user needs to decide what type of data is to be used as the training data, and to prepare a representative real-world set of data.

The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalized function, for example whether to use support vector machines or decision trees. The use of unsupervised or semi-supervised machine learning approaches are sometimes used when labelled data is not readily available, or where the system generates new labelled data from unknown data given some initial seed labels.

The instant disclosure seeks to provide systems and methods to track and monitor persons. FIG. 1 depicts a block diagram of a system, generally 100, for tracking and monitoring persons, according to some embodiments. The system 100 preferably uses machine learning to track and/or monitor persons. The system 100 includes one or more of a server 105, a wireless access point (WAP) 125, a wearable computing device (WCD) 140, computing device 135, and user computing device (UCD) 160. A network 101 interconnects the server 105, a WAP 125, the computing device 135, and the UCD 160. The network 101 can be, for example, a local area network (LAN), a wide area network (WAN) such as the Internet, or a combination of the two, and can include wired, wireless, or fiber optic connections. In general, the network 101 can be any combination of connections and protocols that support communications between the server 105, a WAP 125, the computing device 135, and the UDC 160.

The WAP 125 and the WCD 140 are communicatively coupled to each other and preferably communicate wirelessly using a radio-frequency band(s) (e.g., HF, LF, UHF, SHF). The WCD 140 is not communicatively coupled to the network 101 or other computing devices connected thereto besides the WAP 125. The server 105, the WAP 125, the computing device 135, and the user computing device 160 can be, but are not limited to, personal computer systems, server computer systems, thin clients, thick clients, handheld or laptop devices, mobile devices, wearable computing devices, multiprocessor systems, microprocessor-based systems, network PCs, minicomputer systems, cluster computers, and distributed cloud computing environments that include any of the above systems or devices.

The UCD 160 includes a user interface ("UI") 165. Users utilize the UI 165 generate information queries (e.g., location inquiries, task completion verification, etc.). In other words, the UI 165 allows users to track and monitor persons that wear the wearable computing device ("WCD") 140. The UI 165 can be downloaded from the primary data store 120 (discussed below). The WCD 140 is preferably a computing device that is worn by a user (e.g., on the wrist, head, torso, or other body part). The WCD 140 is configured to be worn by a user (e.g., users 205 and 210) and generate primary input data associated with the user. The primary input data preferably comprises a userID of the user that is wearing the WCD 140. The WCD 140 preferably includes a transponder 145 and at least one sensor 150. The WCD 140 is configured to transmit the primary input data to the WAP 125 when interrogated via the WAP 125.

For example, the transponder 145 receives the interrogation signal from the interrogation device 135 of the WAP 125. The sensor(s) 150 can include one or more accelerometers, magnetometers, geolocation sensors, and similar sensors to capture motion data. In other words, the WCD 140 is preferably configured to capture motion data that reflects one or more dispositions of the user that wears the device. The motion data includes orientation data, velocity data, and/or positional data. The WCD 140 generates primary input data that is associated with the user (e.g., a userID). In other words, the primary input data includes the userIDs and, in some embodiments, the motion data as well. For example, the userID can be a character string that is unique that a particular user (e.g., patient, caregiver, staff member, and similar persons that require tracking and/or monitoring).

The transponder 145 is configured to transmit a response signal to the WAP 125 when it receives an interrogation signal from the WAP 125 (e.g., via the interrogation device 135). For example, the response signal includes a plurality of information (e.g., the primary input data). The WAP 125 is a computing device that transmits interrogation signals (e.g., to WCD 140). The WAP 125 preferably include a camera 130 that is configured to capture a picture(s) of a location (e.g., location 200 of FIG. 2). For example, the location can be a room or similar enclosure where a desired task(s) takes place. In some embodiments, the camera 130 is configured to capture time-of-flight data. The WAP 125 is configured to transmit the primary input data (i.e. data received from the WCD 140) and the secondary input data (i.e. data generated by the WAP 125) to a secondary data store 140 that is included in the computing device 135. In certain embodiments, the WAP 125 and the computing device 135 are a single unit. The WAP 125 and the computing device 135 are preferably positioned at the same location. However, the WAP 125 and the computing device 135 can be positioned at different locations.

The server 105 preferably includes the primary data store 120 and the communications device 115 interconnected via the control circuit 110. The control circuit 110 is one or more processors that can each perform one or more of the steps, processes, methods, and/or functions disclosed herein. The primary data store 120 includes reference data that reflects one or more completed tasks. The reference data contains information that can be used with machine learning to accurately predict desired output values of tasks. The primary data store 120 can include a downloadable copies of the UI 165.

Figure 2:
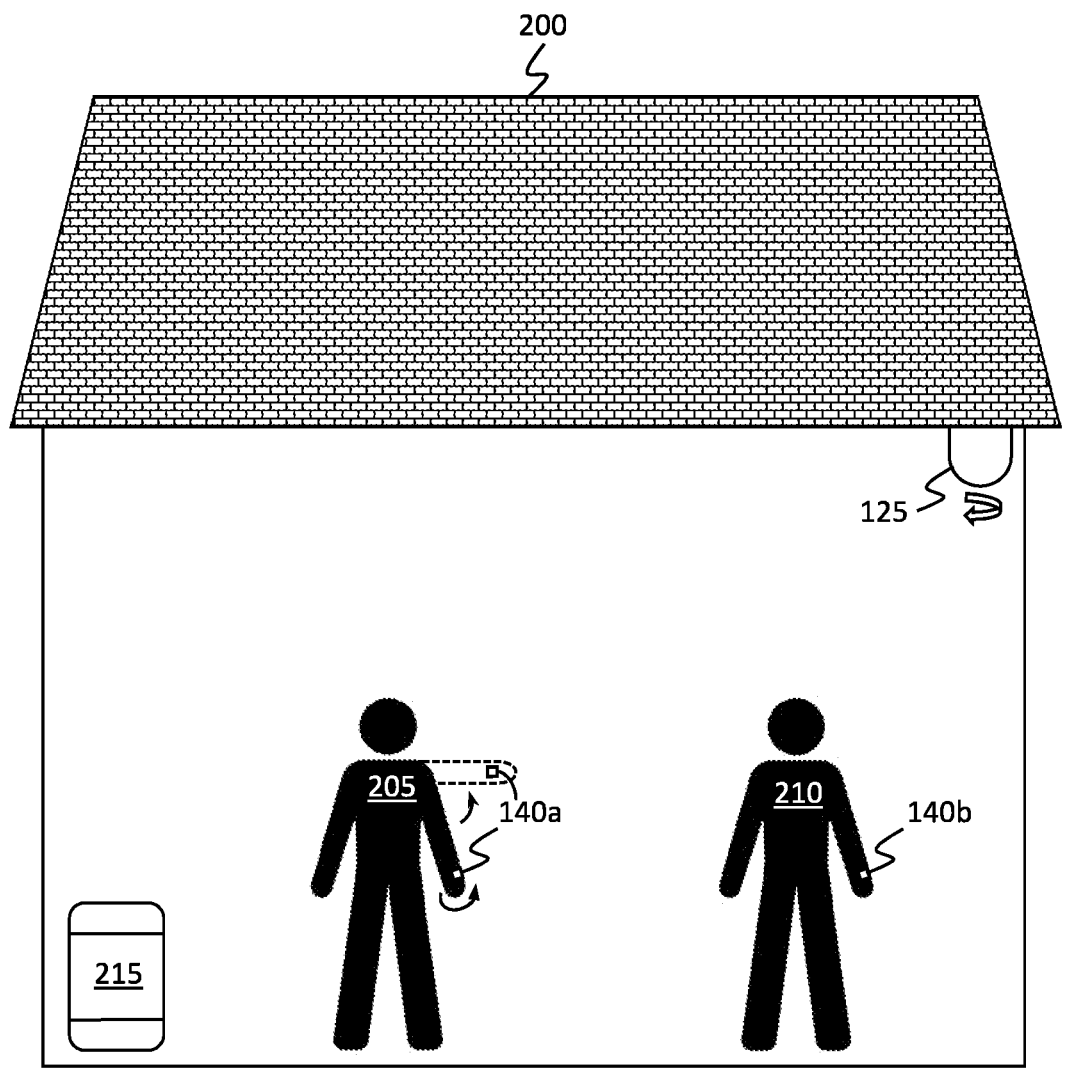
FIG. 2 depicts a side view of a location and a wireless access point positioned therein, according to other embodiments.

FIG. 2 depicts a side view of a location, generally 200, and the WAP 125 positioned therein, according to other embodiments. The WAP 125 is depicted as a structure coupled to the ceiling of the location 200 and communicatively coupled to the WCD 140 (i.e. the WCD 140a and the WCD 140b). The WAP 125 generates secondary input data that is associated with the user(s) (e.g., the user 205 and the user 210) and receives primary input data from the WCD 140 (e.g., the WCD 140a and the WCD 140b). The WCD 140 monitors the disposition of the user. For example, the WCD 140a can use the sensor 150 to monitor user arm rotation and/or elevation. To be sure, the user's position and associated motion data can be analyzed using one or more machine learning algorithm to determine if tasks are completed. The machine learning algorithm can be unsupervised or semi-supervised.

The machine learning algorithm is preferably used to analyze the primary input data and/or the secondary input data to determine if one or more tasks are completed. For example, the machine learning algorithm can be used to map the reference data to the primary data and/or the secondary input data to determine if a task(s) is completed. In other embodiments, the machine learning algorithm utilizes reinforcement learning where the reference data is captured from the environment the machine learning algorithm is exposed to. The sensor 150 can monitor heart rate and/or capture motion data (discussed above). In some embodiments, the sensor 150 can be an accelerometer, a magnetometer, and/or a geolocation sensor (e.g., GPS). The sensor 150 can be a plurality of sensors that function as a single device. To be sure, the WCD 140 can include one or more of the sensor 150.

To generate the secondary input data, the WAP 125 uses the camera 130 to capture one or more pictures (e.g., stills and/or video) of the location 200. The one or more pictures include images of the object 215, the user 205, and the user 210. The WAP 125 interrogates the WCD 140a and the WCD 140b and receives their response signals (i.e. the primary input data) in return.

Figure 3:
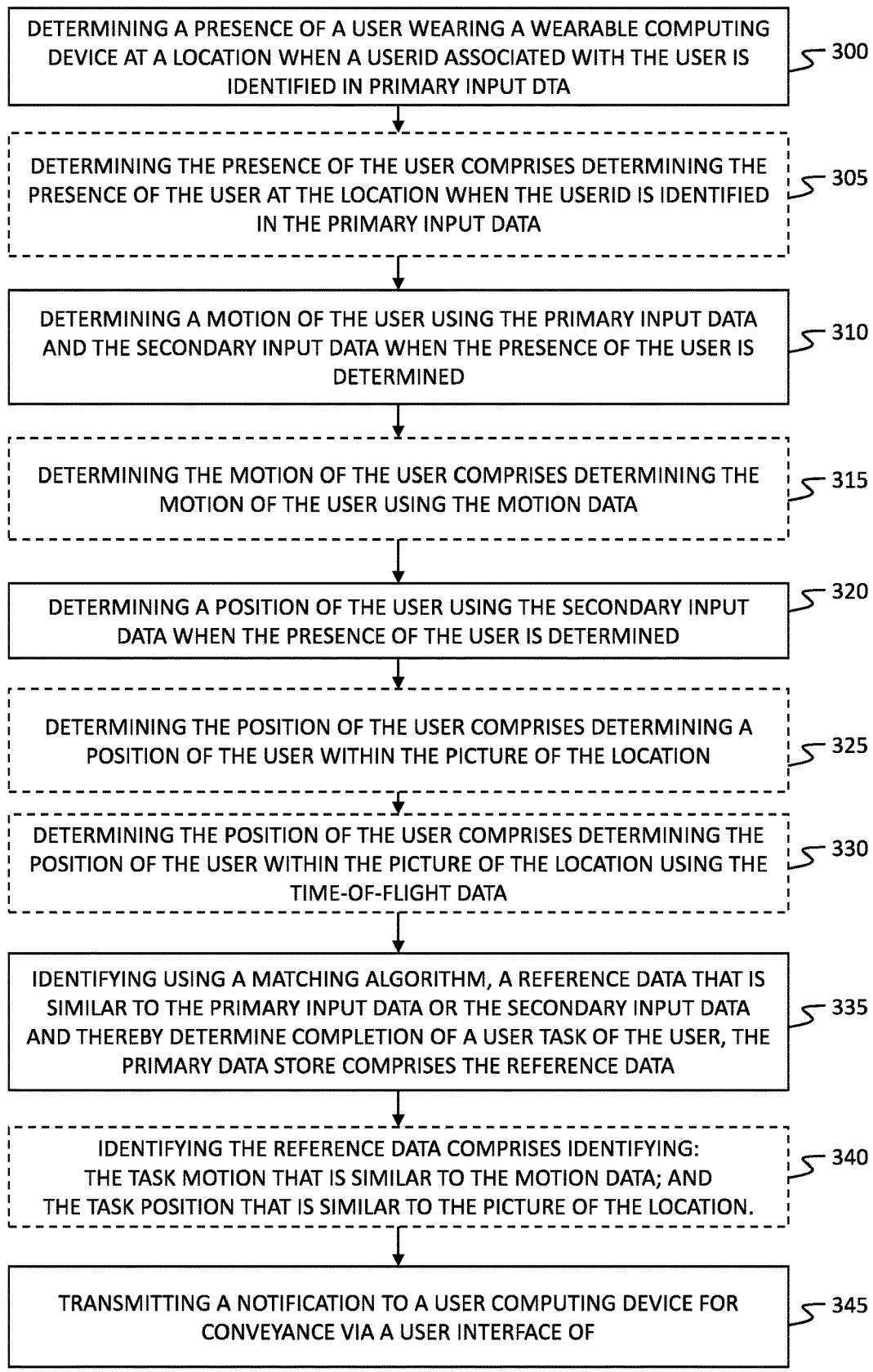
FIG. 3 depicts the process steps of a method to track and monitor persons according to certain embodiments.

FIG. 3 depicts the process steps of a method to track and monitor persons according to certain some embodiments. FIG. 2 will be used in the discussion of FIG. 3. At Step 300, a presence of a user (e.g., the user 205 or the user 210) wearing a WCD 140 at a location (e.g., the location 200) is determined when a userID that is associated with the user(s) is identified in primary input data. For example, at Step 305, to determine the presence of the user includes the presence of the user at the location is determined when the userID is identified in the primary input data. At Step 310, a motion of the user is determined using the primary input data and the secondary input data when the presence of the user is determined. For example, at Step 315, the motion of the user is determined using the motion data.

At Step 320, a position of the user is determined using the secondary input data when the presence of the user is determined. For example, at Step 325, a position of the user is determined within the picture of the location. At Step 330, for example, the position of the user within the picture of the location is determined using the time-of-flight data (e.g., captured via the camera 130). At Step 335, a reference data (e.g., associated with the task) is identified, using a matching algorithm, that is similar to the primary input data or the secondary input data and thereby determine completion of a user task of the user, the primary data store 120 comprises the reference data. For example, identifying the reference data includes identifying the task motion that is similar to the motion data and/or the task position that is similar to the picture of the location.

FIG. 6 depicts a block diagram of components of server 105, the WAP 125, the WCD 140, and the computing devices 135 and 160, in accordance with certain embodiment. Data processing system 400, 500 is representative of any electronic device capable of executing machine-readable program instructions. Data processing system 400, 500 may be representative of a smart phone, a computer system, PDA, or other electronic devices. Examples of computing systems, environments, and/or configurations that may represented by data processing system 400, 500 include, but are not limited to, personal computer systems, server computer systems, thin clients, thick clients, wearable computer, hand-held or laptop devices, multiprocessor systems, microprocessor-based systems, network PCs, minicomputer systems, and distributed cloud computing environments that include any of the above systems or devices.

Figure 4:
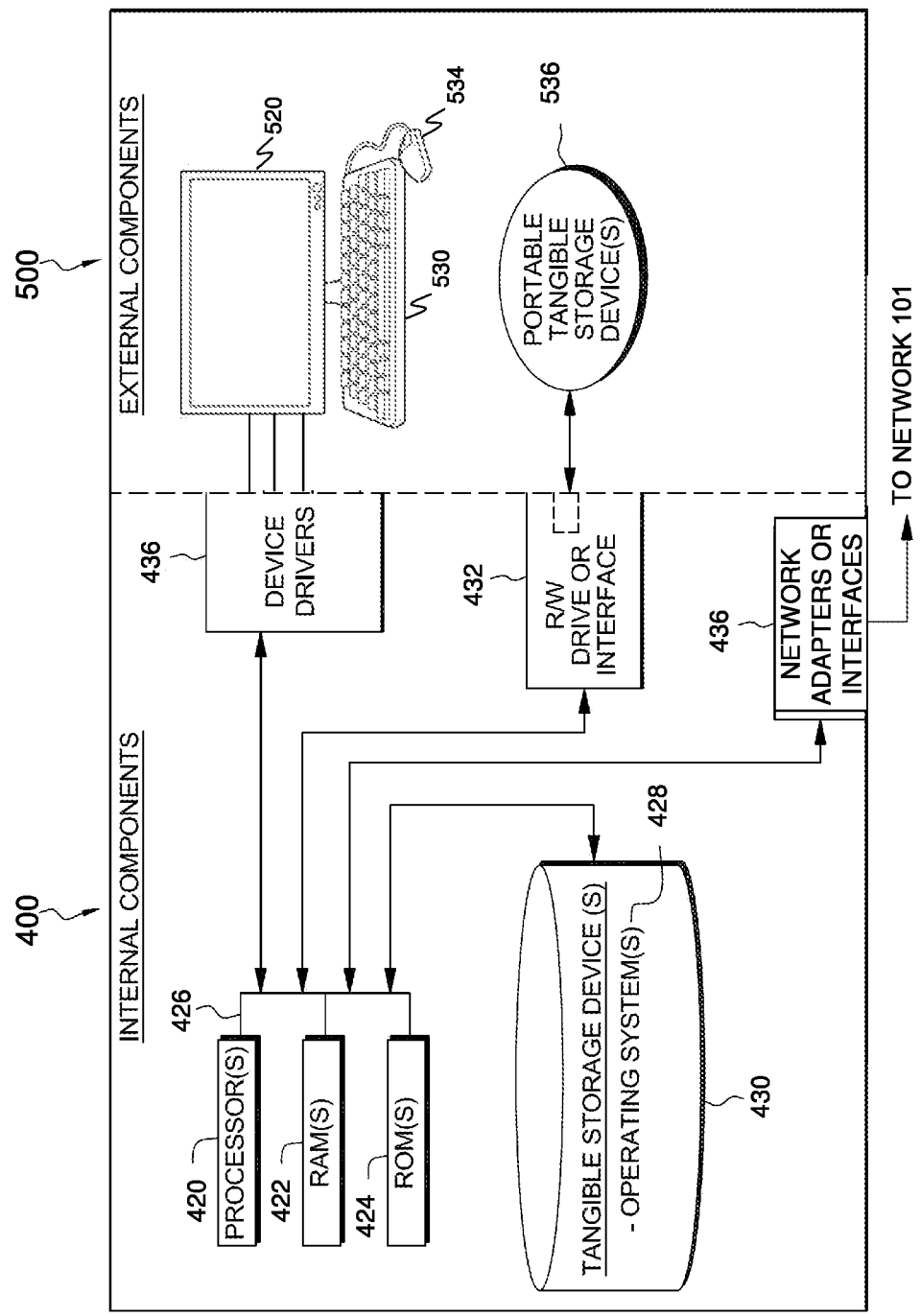
FIG. 4 depicts a block diagram of components of a computing device, in accordance with yet still others embodiments.

The server 105, the WAP 125, the WCD 140, as well as the computing devices 135 and 160 can each include respective sets of internal components 400 and external components 500 as illustrated in FIG. 4. Each of the sets of internal components 400 includes one or more processors 420, one or more computer-readable RAMs 422 and one or more computer-readable ROMs 424 on one or more buses 426, and one or more operating systems 428 and one or more computer-readable tangible storage devices 430. One or more of program function and data files (e.g., the primary input data and the secondary input data) are stored on one or more of the respective computer-readable tangible storage devices 430 for execution by one or more of processors 420 via one or more of the respective RAMs 422 (which typically include cache memory).

In the embodiment illustrated in FIG. 4, each of the computer-readable tangible storage devices 430 is a magnetic disk storage device of an internal hard drive. Alternatively, each of the computer-readable tangible storage devices 430 is a semiconductor storage device, such as ROM 424, EPROM, flash memory or any other computer-readable tangible storage device that can store a computer program and digital information.

Internal components 400 also include a R/W drive or interface 432 to read from and write to one or more portable computer-readable tangible storage devices 536, such as a CD-ROM, DVD, memory stick, magnetic tape, magnetic disk, optical disk or semiconductor storage device. Program functions and data files (e.g., the primary input data and the secondary input data) can be stored on one or more of the respective portable computer-readable tangible storage devices 536, read via the respective R/W drive or interface 432 and loaded into the respective computer-readable tangible storage devices 430.

Each set of internal components 400 also includes network adapters or interfaces 436 such as a TCP/IP adapter cards, wireless Wi-Fi interface cards, or 3G or 4G wireless interface cards or other wired or wireless communication links. Program functions and data files (e.g., the primary input data and the secondary input data) can be downloaded, respectively, from an external computer via a network (for example, the Internet, a local area network or other, wide area network) and respective network adapters or interfaces 436. From the network adapters or interfaces 436, program function and data files in each of the disclosed devices are loaded into the respective computer-readable tangible storage devices 430. The network may comprise copper wires, optical fibers, wireless transmission, routers, firewalls, switches, gateway computers and/or edge servers.

Each of the sets of external components 500 can include a computer display monitor 520, a keyboard 530, and a computer mouse 534. External components 500 can also include touch screens, virtual keyboards, touch pads, pointing devices, and other human interface devices. Internal components 400 also include device drivers 440 to interface to computer display monitor 520, keyboard 530 and computer mouse 534. The device drivers 440, R/W drive or interface 432 and network adapters or interfaces 436 comprise hardware and software (stored in storage device 430 and/or ROM 424). Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, though the Internet using an Internet Service Provider).

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the disclosure has been explained in relation to its preferred embodiment, it is to be understood that many other possible modifications and variations can be made without departing from the spirit and scope of the disclosure.

The invention claimed is:

1. A system for tracking and monitoring persons, comprising: a user computing device ("UCD") that comprises a user interface; a wearable computing device ("WCD') configured to be worn by a user and generate primary input data associated with the user, the primary input data comprises a userID of the user;
  a wireless access point ("WAP") positioned at a location, communicatively coupled to the WCD, configured to generate secondary input data associated with the user and receive primary input data from the WCD;
  a control circuit communicatively coupled to the UCD and a primary data store that comprises reference data;
  wherein the WCD is configured to transmit the primary input data to the WAP when interrogated via the WAP;
  wherein the WAP is configured to transmit the primary input data and the secondary input data to a secondary data store;
  wherein the control circuit is communicatively coupled to the secondary data store and configured to:
  determine a presence of the user at the location when the userID is identified in the primary input data;
  determine a motion of the user using the primary input data and the secondary input data when the presence of the user at the location is determined;
  determine a position of the user using the secondary input data when the presence of the user is determined;
  identify, using a matching algorithm, the reference data that is similar to the primary input data or the secondary input data and thereby determine completion of a user task of the user; and
  transmit, via a communications device communicatively coupled to the control circuit, a notification to the UCD for conveyance via the user interface when completion of the user task is determined;
  wherein the WAP comprises a camera that is configured to capture a picture of the location;
  the camera is configured to capture time-of-flight data;
  the picture of the location comprises the time-of-flight data; and
  in determining the position of the user, the control circuit is configured to determine the position of the user within the picture of the location using the time-of-flight data.

2. The system of claim 1, wherein
  the WAP is configured to transmit an interrogation signal;
  the WCD comprises a transponder configured to transmit a response signal to the WAP in response to receiving the interrogation signal;
  the response signal comprises the primary input data; and
  in determining the presence of the user, the control circuit is configured to determine the presence of the user at the location when the userID is identified in the primary input data.

3. The system of claim 2, wherein
  the WCD is configured to capture motion data associated with a disposition of the user;
  the motion data comprises one or more of orientation data, velocity data, and positional data;
  the primary input data comprises the motion data; and in determining the motion of the user, the control circuit is configured to determine the motion of the user using the motion data.

4. The system of claim 3, wherein
the secondary input data comprises the picture of the location; and in determining the position of the user, the control circuit is configured to determine a position of the user within the picture of the location.

5. The system of claim 4, wherein
the reference data comprises a task motion and/or a task position associated with completion of the user task;
in identifying the reference data, the control circuit is configured to identify the reference data by identifying, using the matching algorithm, one or more of: the task motion that is similar to the motion data; and
the task position that is similar to the picture of the location.

6. The system of claim 5, wherein the WCD comprises one or more of an accelerometer, a magnetometer, and a geolocation sensor.

7. A method to track and monitor persons, comprising:
determining, via a control circuit communicatively coupled to a primary data store and a secondary data store, a presence of a user wearing a wearable computing device ("WCD") at a location when a userID associated with the user is identified in primary input data, the WCD generates the primary input data and is communicatively coupled to a wireless access point ("WAP") positioned at the location, the WCD transmits the primary input data to the WAP when interrogated via the WAP, the WAP generates secondary input data associated with the user and receives primary input data from the WCD, the WAP transmits the primary input data and the secondary input data to the secondary data store;
determining, via the control circuit, a motion of the user using the primary input data and the secondary input data when the presence of the user is determined;
determining, via the control circuit, a position of the user using the secondary input data when the presence of the user is determined;
identifying, via the control circuit, using a matching algorithm, a reference data that is similar to the primary input data or the secondary input data and thereby determine completion of a user task of the user, the primary data store comprises the reference data; and
transmitting, via the communications device communicatively coupled to the control circuit, a notification to a user computing device for conveyance via a user interface of the user computing device when the completion of the user task is determined;
wherein the WAP comprises a camera that is configured to capture a picture of the location;
the camera is configured to capture time-of-flight data;
the picture of the location comprises the time-of-flight data; and
in determining the position of the user, the control circuit is configured to determine the position of the user within the picture of the location using the time-of-flight data.

8. The method of claim 7, wherein
the WAP transmits an interrogation signal;
the WCD comprises a transponder that transmits a response signal to the WAP in response to receiving the interrogation signal;
the response signal comprises the primary input data; and
determining the presence of the user comprises determining, via the control circuit, the presence of the user at the location when the userID is identified in the primary input data.

9. The method of claim 8, wherein
the WCD captures motion data associated with a disposition of the user; the motion data comprises one or more of orientation data, velocity data, and position data;
the primary input data comprises the motion data; and
determining the motion of the user comprises determining, via the control circuit, the motion of the user using the motion data.

10. The method of claim 9, wherein
the secondary input data comprises the picture of the location; and determining the position of the user comprises determining, via the control circuit, a position of the user within the picture of the location.

11. The method of claim 10, wherein
the reference data comprises a task motion and/or a task position associated with completion of the user task;
identifying the reference data comprises identifying, via the control circuit, one or more of the following using the matching algorithm:
the task motion that is similar to the motion data; and the task position that is similar to the picture of the location.

* * * * *